US007008774B2

(12) United States Patent
Ryan et al.

(10) Patent No.: US 7,008,774 B2
(45) Date of Patent: Mar. 7, 2006

(54) PRACTICAL SEROLOGICAL ASSAY FOR THE CLINICAL DIAGNOSIS OF LEISHMANIASIS

(75) Inventors: Jeffrey R. Ryan, Reston, VA (US); Samuel K. Martin, Burtonsville, MD (US); Anthony M. Smithyman, Collaroy (AU)

(73) Assignee: The United States of America as represented by the Secretary of the Army, Washington, DC (US)

( * ) Notice: Subject to any disclaimer, the term of this patent is extended or adjusted under 35 U.S.C. 154(b) by 143 days.

(21) Appl. No.: 10/173,586

(22) Filed: Jun. 18, 2002

(65) Prior Publication Data

US 2003/0008332 A1 Jan. 9, 2003

Related U.S. Application Data

(63) Continuation of application No. 09/725,182, filed on Nov. 29, 2000, now abandoned.

(60) Provisional application No. 60/168,300, filed on Dec. 1, 1999, now abandoned.

(51) Int. Cl.
*G01N 33/53* (2006.01)
*C12Q 1/70* (2006.01)
*C12Q 1/69* (2006.01)
*A61K 30/005* (2006.01)
*C07K 14/00* (2006.01)

(52) U.S. Cl. .............................. 435/7.1; 435/5; 435/6; 435/7.22; 424/269.1; 424/93.1; 530/350

(58) Field of Classification Search ................ 435/7.1, 435/7.22, 5, 6, 91.2, 975, 258.1; 424/269.1, 424/93.1, 93.2, 93.4, 186.1; 530/350, 364, 530/806
See application file for complete search history.

(56) References Cited

U.S. PATENT DOCUMENTS

6,197,757 B1 * 3/2001 Perrier et al. .................. 514/53

FOREIGN PATENT DOCUMENTS

WO         WOX 99/56755       * 11/1999

OTHER PUBLICATIONS

Ryan et al 1999; Am.J.Trop.Med.Hyg; 61; No: 3 p. 456 abstract from conference.*
Wirtz et al 1989, Bulletin of the World Health Organization 1989, 67/5, 535-542.*
Merlen et al 1999; Am.J.Trop.Med.Hyg; 60; 41-50.*
Arora et al; Indian Journal of Parasitology 1984, 8, 97-98.*
R. Badario, D. Benson, M.C. Eulalio, M. Freire, S. Cunha, E.M. Netto, D. Pedral-Sampaio, C. Madureira, J. M. Burns, R. L. Houghton, J. R. David, and S. G. Reed rK39: A Cloned Antigen of *Leishmannia chagasi* that Predicts Active Visceral, JID, 1996, 173:758-761.
R. Badaro, S. Reed, A. Barral, G. Orge, and T. Jones, Evaluation of the Micro Enzyme-Linked Immunosorbent Assay (Elisa) for Antibodies in Selection for Detection of Infection-Specific Responses, Am. J. Trop. Med. Hyg., 1986, 35(1) 72-78.
P. A. Bates, M. Kurtz, M. Gottlieb, and D. M. Dwyer, *Leishmania donovani*: Generation of Monospecific Antibody Regents to Soluble Acid Phosphatase, Experimental Parasitology 1987, 64:157-164.
P. A. Bates, M. Gottlieb, and D. M. Dwyer, *Leishmania donovani* : Identification of Glycoproteins Released by Promastigotes during Growth in Vitro, Experimental Parasitology, 1988, 67:199-209.
R. S. Bray and R. Lainson, The Immunology and Serology of Leishmanisis IV. Results of Ouchterlony Double Diffusion Tests, Transactions of the Royal society of Tropical Medicine and Hygiene, 60(5) 1966.
A. Choudhry, P. Y. Guru, R. P. Saxena, A. Tandon, and K. C. Saxena, Enzyme-linked immunosorbent assay in the Diagnosisi of Kala-Azar in Bhodohi (Varanasi), India, Transactions of the Royal Society of Tropical Medicine and Hygiene, 1990 84:363-366.
A. Choudhry, A. Puri, P. Y. Guru, R. P. Sexena, and K. C. Saxena, An Indirect Fluorescent Antibody (IFA) Test for the Serodiagnosis of Kala-Azar, J. Com. Dis., 1992, 24(1):32-36.
S. L. Ellis, A. M. Shankarian, and D. M. Dwyer, *Leishmania*: Amastigotes Synthesize Conserved Secretory Acid Phosphates during Human Infection, Experimental Parasitology, 1998, 89:161-168.
J. El-On, L. F. Schnur, and C. L. Greenblatt, *Leishmania donovani*: Physicochemical, Immunological, and Biological Characterization of Excreted Factor from Promastigotes, Expermental Parasitology, 1979, 47:254-269.

(Continued)

*Primary Examiner*—Lynette R. F. Smith
*Assistant Examiner*—Padma Baskar
(74) *Attorney, Agent, or Firm*—Elizabeth Arwine (57) ABSTRACT

Methods for the diagnosis of visceral, cutaneous and canine leishmaniasis in a subject suspected of being infected with the parasitic protozoa *Leishmania* is disclosed. Disclosed are antibody-capture enzyme-linked immunosorbent assays (ELISAs) for the detection of antibodies to *Leishmania* parasite soluble antigens and antigen-capture ELISAs for the detection of *Leishmania* parasite soluble antigens in host samples. Also disclosed are immunodiagnostic kits for the detection of *Leishmania* parasite circulating antigens or IgM and IgG antibodies in a sample from subject having visceral, cutaneous or canine leishmaniasis. In these methods and kits, detection may be done photometrically or visually. The methods and kits also allow the visualization of *Leishmania* amastigotes or promastigotes in a sample.

20 Claims, 9 Drawing Sheets

OTHER PUBLICATIONS

M. del R. Garcia-Miss, F. J. Andrade-Narvaez, R. E. Esquivel-Vinas, E. B. Simmonds-Diaz, B. Canto-Lara, and L. Cruz-Ruiz, Transactions of the Royal Society of Tropical Medicine and Hygiene, 1990, 84:356-358.

K. D. Greis, and S. J. Turco, Purification and Characterization of an Extracellular Phosphoglycan from *Leishmania donovani*, The Journal of Biological Chemistry, Mar. 25, 1992, 267(9);5876-5881.

S. K. Martin, L. Thuita-Harun, M. Adoyo-Adoyo and K. M. Wasunna; A Diagnostic ELISA for Visceral Leishmaniasis, based on Antigen form Media Conditioned by *Leishmania donovani* promastigotes, Annals of Tropical Med. & Parasitology, 1998 92(5): 571-577.

S. G. Reed, W. G. Shreffler, J. M. Burns, Jr., J. M. Scott, M. G. Orge, H. W. Ghalib, M. Sidding, and R. Badaro, An Improved Serodiagnostic Procedure for Visceral Leishmaniasis, Am. J. Trop. Med. Hyg., 1990, 43(6):632-639.

J. L. Sanchez, B. M. Diniega, J. W. Small, R. N. Miller, J. M. Andujar, P. J. Weina, P. G. Lawyer, W. R. Ballou and J. K. Lovelace, Am. J. Rtop Med. Hyg., 1992, 47(1):47-54.

L. F. Schnur, M.sc., A. Zuckerman, Ph.D., and C. L. Greenblatt, M.D., Leishmanial Serotypes as Distinguished by the Gel Diffusion of Factors Excreted In Vitro and In Vivo, Isrl. J. Med. Sci., 1972, 8(7):932-942.

G. Senaldi, H. Xio-su, D.C. Hoessil, C. Bordier, Serological Diagnosis of Visceral Leishmaniasis by a Dot-enzyme Immunoassay for the Detection of a *Leishmania donovani*-related Circulating Antigen, Journal of Immunological Methods, 1996, 193:9-15.

Sergeiev, V. P., et al., Med. Parasitol., 1995, 38:208-212.

E. E. Zijlstra, O. F. Osman, H. W. Chr. Hofland, L. Oskam, H. W. Ghalib, A. M. El-Hassan, P. A. Hager, and S. E. O. Meredith, Transactions of the Royal Society of Tropical Medicine and Hygiene, 1997 91:671-673.

* cited by examiner

Figure 1: Specific Ab Levels (IgG) in Visceral Leishmaniasis Patients

Figure 5: Specific Ab Levels (IgG) in Canines Infected with *L. chagasi*

Figure 6: Specific Ab Levels (IgM) in Canines Infected with *L. chagasi*

Figure 7: Western blot showing specific activity of Rabbit anti-leishmania PAb, normal human sera and sera from kala azar patients.

Figure 8: Graph Depicting Specific Activity of the Competitive Ag-Capture ELISA Using Different Antigen and HRP-Labeled Antigen Conditions.

Figure 9: Graph Depicting Specific Activity of the Competitive Ag-Capture ELISA While Titrating Labeled Antigen Under Different Coating and Blocking Conditions

PRACTICAL SEROLOGICAL ASSAY FOR THE CLINICAL DIAGNOSIS OF LEISHMANIASIS

RELATED APPLICATION DATA

This application is a continuation of U.S. Utility patent application Ser. No. 09/725,182, filed 29 Nov. 2000, abandoned which claims the benefit of U.S. Provisional Patent Application Ser. No. 60/168,300, filed 1 Dec. 1999, abandoned naming Jeffrey R. Ryan, Samuel K. Martin, and Anthony M. Smithyman as joint inventors, all of which are herein incorporated by reference.

ACKNOWLEDGMENT OF GOVERNMENT SUPPORT

This invention was made by employees of the United States Army. The government has rights in the invention.

BACKGROUND OF THE INVENTION

1. Field of the Invention

This invention relates generally to a method of diagnosing leishmaniasis in a subject suspected of being infected with the parasitic protozoa *Leishmania*. In particular, the invention relates to enzyme-linked immunosorbent assays (ELISAs) for the detection of *Leishmania* parasite circulating antigens and *Leishmania*-specific antibodies in host samples.

2. Description of the Related Art

*Leishmania* sis is a serious and sometimes fatal disease estimated by the World Health Organization (WHO) to affect approximately 12 million people in 88 countries. Recent epidemics of leishmaniasis have occurred in the Africa, the Indian subcontinent and Brazil. In addition to the concerns regarding significant morbidity and mortality caused by leishmaniasis in endemic areas, the increase in global travel concomitant with the increased incidence of the disease in HIV-infected and intravenous drug-user populations is a cause for concern in non-endemic areas more recently.

Unfortunately, current acceptable diagnostic practices lack the means for efficiently and accurately identifying those infected or exposed to the disease-causing parasite as explained in Martin, S. et al. (1998) Military Medicine 163(23):801–807. As a result, the prevention of leishmanial epidemics is greatly hindered and patient management is difficult. Additionally, there is an imminent threat of a developing population of people co-infected with HIV and *Leishmania*. To date, there are no antigen-detection type diagnostic tests available for Leishmaniasis. In view of this, antigen-detection assays are desperately needed for diagnosis, patient management and epidemiological studies.

Recombinant kinesin protein, rK39, is one of the few antigens that has been used in the development of antibody-detection immunoassays for active visceral leishmaniasis (VL). However, assays of this antigen and others fail to consistently detect antibodies in other clinical syndromes associated with a predominately T-cell and muted B-cell response. Moreover, antibody-detection assays have an inherent limitation—dependence on the immune response of the host to the parasite antigen. For example, in an immunocompromised host, the infection may not produce proportional antibody production and thereby escape detection. Generally, the serological tests for diagnosing VL are highly sensitive (>90%). See Senaldi, G., et al., (1996) J. Immunol. Methods 193:9–5. These serological tests, however, pose problems of non-specificity resulting in false positive results from reference samples of other infectious diseases and subclinical leishmanial infections. Modifications of the antigens used for direct agglutination test (DAT) and for ELISA are reported to be markedly successful in eliminating false-positive results. See Zijlstra, E. E., et al., (1997) Trans. R. Soc. Trop. Med. Hyg. 91:671–673 and Badaro, R., et al., (1996) J. Inf. Dis. 173:758–761. Unfortunately, serological tests are rarely performed to diagnose cutaneous leishmaniasis because the sensitivities and specificities are disappointingly poor for that clinical manifestation. See Sanchez, J. L., et al., (1992) Am. J. Trop. Med. Hyg. 47:47–54; Garcia-Miss, M. R., et al., (1990) Trans. R. Soc. Trop. Med. Hg. 84:356–358.

The antigens used in immunoassays for the detection of leishmaniasis are traditionally derived from promastigotes cultivated in vitro, or from recombinant proteins. See Badaro et al. (1996); Choudhary, S., et al., (1992) J. Comm. Dis. 24:32–36; Badaro, R., et al., (1986) Am. J. Trop. Med. Hyg. 35:72–78; Choudhary, A., et al., (1990) Trans. R. Soc. Trop. Med. Hyg. 84:363–366; and Reed, S. G., et al., (1990) Am. J. Trop. Med. Hyg. 43:632–639. The promastigotes release metabolic products into the culture medium to produce conditioned medium. These metabolic products are immunogenic to the host. See Schnur, L. F., et al., (1972) Isrl. J. Med. Sci. 8:932–942; Sergeiev, V. P., et al., (1969) Med. Parasitol. 38:208–212; El-On, J., et al., (1979) Exper. Parasitol. 47:254–269; and Bray, R. S., et al., (1966) Trans. R. Soc. Trop. Med. Hyg. 60:605–609.

The prior art assays are based on these metabolic products found in the in vitro culture medium. Thus, the presence of complex proteins or serum components required for growth of the parasites in culture pose several problems in the prior art assays. For example, the amount of manipulation needed to purify the targeted antigens from the metabolic products can affect the native composition of certain components necessary for a highly sensitive assay. Furthermore, insufficient purification techniques may create problems with specificity as common proteins remain in the antigen preparations, which cause non-specific reactions. Generally, the prior art assays are limited in scope to one species complex or clinical manifestation and have never demonstrated combined sensitivity and specificity of more than 90%.

Thus, a need exists for highly sensitive and highly specific assays for detecting, measuring, or diagnosing exposure to *Leishmania*.

SUMMARY OF THE INVENTION

The invention relates to an immunoassay for detecting IgM and IgG antibodies in a sample from a subject having visceral, cutaneous or canine leishmaniasis.

The invention also relates to an immunoassay for detecting *Leishmania* parasite circulating antigens in a sample from a subject having visceral, cutaneous or canine leishmaniasis.

In one embodiment, the invention relates to a leishmaniasis immunoassay, which is based on soluble antigens from promastigotes cultivated in a protein-free and serum-free medium.

In another embodiment, the invention relates to the use of protein-free and serum-free medium to cultivate the promastigotes in an immunoassay for the diagnosis of leishmaniasis.

In a preferred embodiment, the assay of the invention has a high degree of sensitivity and specificity. For example, the assay of the invention has a combined sensitivity and specificity of more than about 90%. Preferably, the assay of the present invention has sensitivity of about 95.1% and a specificity of about 100%.

The invention also relates to an antigen-capture immunoassay for the detection of exo-antigens released by the parasite in a sample from subject having visceral, cutaneous or canine leishmaniasis.

The invention also relates to immunodiagnostic kits for the detection of specific IgM and IgG antibodies to *Leishmania* parasite circulating antigens in a sample from a subject having visceral, cutaneous or canine leishmaniasis. Detection may be done photometrically or visually. If visual detection is desired, a fluorescent chromogenic or chemiluminescent agent may be utilized. Preferably, the intensity or amount of the visual signal is in proportion to the amount of the antibody present in the sample.

In one embodiment, the invention allows the visualization of *Leishmania* amastigotes or promastigotes by the use of a fluorescein conjugated polyclonal antibody to the specific antigen preparation aforementioned.

Preferably, the protein-free and serum-free medium utilized in the present invention comprises a cross-linking agent that is not metabolized by cultures and is relatively easy to purify out by dialysis. In a preferred embodiment of the invention the medium comprises xylose as xylose is not metabolized by cultures. Additionally, only small amounts of xylose are required. Since only small amounts of xylose are necessary, purification is relatively easy and less destructive to the components found in the conditioned medium.

DESCRIPTION OF THE DRAWINGS

This invention is further understood by reference to the drawings wherein.

DETAILED DESCRIPTION OF THE INVENTION

Recently, the soluble antigens shed, excreted and secreted by *Leishmania* parasites in a protein-free medium have been described. The soluble antigens of *L. donovani* promastigotes, are primarily lipophosphoglycan (LPG), and comprise an albumin binding site, a hydrophilic LPG component, and a repeating phosphorylated saccharide linked with secreted acid phosphatase (S-AcP). See Greis, K. D., et al., (1992) J. Biol. Chem. 267:5876–5881. S-AcP is presumably the most immunogenic of all the glycoproteins and is a major component in *L. donovani* promastigote conditioned medium. See Bates, P. A., et al., (1988) Exper. Parasitol. 67:199–209. Monoclonal antibody (MAb) studies show no cross reactivity between S-AcP and parasite surface membrane or host acid phosphatases. See Bates, P. A., et al., (1987) Exper. Parasitol. 64:157–164. S-AcP from *L. donovani* promastigote conditioned medium has been used to immunoprecipitate specific antibody from pooled sera of patients acutely ill with VL (kala-azar). See Ellis, S. L., et al., (1998) Exp. Parasitol. 89:161–168.

The use of a soluble antigen preparation from *Leishmania donovani* to capture specific IgG antibodies in the sera of kala-azar patients indicates that the soluble antigens found in conditioned medium can act as the foundation for leishmaniasis immunoassays. See Martin et al. (1998) An. Trop. Med. & Parasit. 92: 571–577.

Thus, the present invention generally relates to leishmaniasis immunoassays, which are highly sensitive and specific and allow the detection of specific IgG and IgM antibodies in subjects affected with visceral, cutaneous, or canine leishmaniasis. The present invention also relates to antigen-capture immunoassays which allow the detection of the soluble *Leishmania* antigens.

The present invention relates to an immunoassay that allows the detection of IgM and IgG antibodies in subjects affected with visceral, cutaneous, or canine leishmaniasis. The assay is based on soluble antigens from promastigotes cultivated in a protein-free and serum-free medium and takes less than four hours to perform.

Prior research attempts employing non-recombinant antigens in the design of serologic tests for leishmaniasis have been limited by problems with sensitivity, specificity and test reproducibility. Reasons for these limitations remain elusive, but are most likely attributable to physical and chemical techniques used in antigen preparation. Therefore, the present invention relates to sensitizing plates with soluble antigens from conditioned media. Plate sensitization ameliorates the prior art problems associated with physical and chemical techniques used in antigen preparation.

In order to obtain soluble antigens from conditioned media, cells must be maintained within defined physiological ranges to thrive in vitro. These conditions include temperature, pH, osmotic pressure, $O_2$ and $CO_2$ gas tension, and nutrients. It has been shown that cells fail to thrive in culture media unless 10 to 20% serum albumin is added and the viability and growth rates are compromised where serum albumin concentrations vary substantially from 10%. It is believed that the primary role of serum albumin in in vivo and in vitro cell culture systems is to balance oncotic pressure across the semi-permeable membrane of cells and to provide free water homeostasis. It is also believed that the critical component of serum for in vitro cell survival is albumin.

Therefore, one aspect of the present invention is the propagation of the promastigotes in serum-free and protein-free medium comprising an agent that balances the oncotic pressure across the semi-permeable membrane of the cells. An example of this agent is xylose. Thus, the uncharacterized soluble factors in conditioned medium from the cultivation of promastigotes in protein-free and serum-free medium can be used as a foundation for an immunoassay for visceral, cutaneous, or canine leishmaniasis. The use of a defined protein-free and serum-free culture medium reduces antigen production to a simple and inexpensive centrifugation step and greatly increases the sensitivity, specificity, reproducibility and practicability of the assay. Additionally, gram quantities of the soluble antigens may be inexpensively and reproducibly generated by methods standard in the art. Furthermore, reactivity to the soluble antigens appears to be genus specific.

Since sensitivity to oncotic imbalance varies with cell type, one may wish to conduct experiments to determine the optimum concentration range of the agent which balances the oncotic pressure across the semi-permeable membrane of a given cell type. For example, parasites may be cultured in a serum-free and protein-free medium, wherein a colloidal agent balances the oncotic pressure. The growth index may be determined by comparing the growth of the parasites in the serum-free and protein-free medium with the growth of the parasites in serum supplemented media. Based on the comparison, one may then choose the optimum concentration range of the colloidal agent.

When attempting to detect specific IgM, normally one must consider the effect of IgG in the sample and compensate for its presence or eliminate it altogether. Thus, a fraction of samples tested (n=100) were subjected to a Rapi-Sep spin column (INDX), which binds the IgG in the samples to the membranes, before testing for specific IgM. There was no significant change in the IgM values derived for any sample.

In preliminary studies, 129 visceral (Brazil, Italy, North Africa, Nepal) and 143 cutaneous (Brazil) leishmaniasis patients with controls were tested. These studies show an overall sensitivity of 95.1% when Leishmania-specific IgG was measured against that of healthy, North American negative controls. No cross-reactivity was noted when this assay was used to look for cross-reacting antibodies in patient samples from other parasitic diseases (malaria, echinococcosis, Africa trypanosomiasis, and filariasis). See Martin et al.

Figure 1:
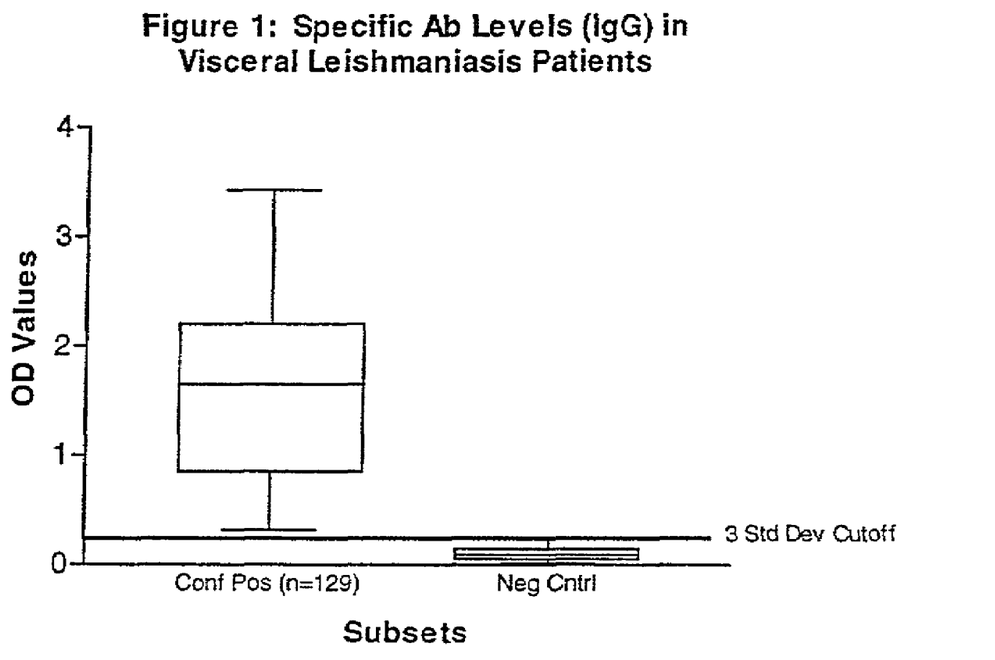
FIG. 1 is a boxplot to illustrate specific IgG antibody levels measured in VL patient sera samples.
Figure 2:
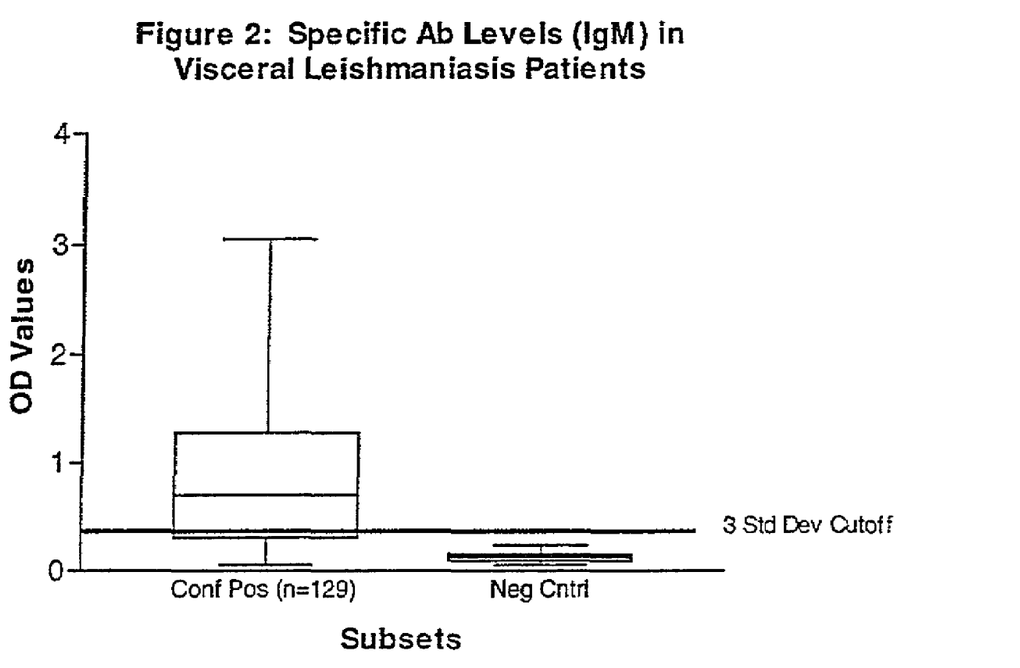
FIG. 2 is a boxplot showing specific IgM antibody levels measured in the same samples.

In additional studies, the assay of the present invention correctly identified 42 sera from Brazilian dogs with canine leishmaniasis and 10 healthy controls. As shown in FIGS. 1–6, the difference between negative and positive was greater in the case of dog sera than of human sera. The negative control sera subset gave a negative cutoff score of about 0.225 for the IgG assay. FIG. 1 is a boxplot to illustrate specific IgG antibody levels measured in VL patient sera samples. With respect to specific IgG, all 129 clinically confirmed positive VL patient sera gave OD readings above the negative cutoff (100% sensitivity). FIG. 2 is a boxplot showing specific IgM antibody levels measured in the same samples. When measuring IgM, the negative control sera tested gave a negative cutoff score of about 0.310. The sensitivity for this assay was 94.57% (122/129 positive).

Currently, the assay is able to detect specific IgG and IgM antibodies with varying degrees of success in patient serum samples from known-positive cases of visceral leishmaniasis (VL) and cutaneous leishmaniasis (CL). The assay may be improved by modifying serum sample and conjugate dilution, substrate, incubation times, temperatures, and other assay conditions, such as described in Example 8, and is well within the skill and knowledge of one of ordinary skill in the art. For example, the serum may be diluted by 1:1000 instead of 1:200 and all incubations may be at room temperature instead of a 37° C. humidity chamber. Serum samples may be diluted from about 1:250 to about 1:1,000. Preferably, for CL assays, the serum sample is diluted to 1:250 and for VL assays, the serum sample is diluted to 1:1,000. The wide range of conjugates that may be produced from polyclonal antibodies against these antigens vary in their affinity and avidity. As such, their working dilutions range from 1:5,000 to about 1:32,000. However, one of ordinary skill in the art may readily determine the optimum dilutions for a given sample and assay by methods standard in the art such as checkerboard titrations.

Initially, all categories of patient samples were tested with the WR0130E L. donovani antigen (ATCC strain 30503). However, the assay was not sensitive to CL patient sera samples. Thus, these CL samples were retested with the L. mexicana (ATCC strain 50157) antigen.

The immunoassay of the present invention may detect IgM and IgG antibodies in human patients with visceral and cutaneous leishmaniasis, and dogs with canine leishmaniasis. When using Leishmania-specific IgG antibodies as a marker for active disease the test showed an overall sensitivity of 95.9% (261/272) and a specificity of 100%.

The following examples are intended to illustrate but not to limit the invention.

EXAMPLE 1

Sera Preparation

Serum was collected from human patients who were admitted to clinics in Brazil, Italy, North Africa, Nepal and Walter Reed Army Medical Center and who had either splenic aspirates or skin biopsies from lesions that tested positive for Leishmania parasites by culture and microscopy. In total, 129 visceral (Italy, Brazil, North Africa, and Nepal) and 143 cutaneous (Brazil) leishmaniasis patients (136-L. braziliensis-infected, and 7 L. panamensis-infected) with controls were tested.

Human negative controls were from 12 non-endemic area normal patients with no documented infection or exposure to Leishmania parasites. In addition to the human manifestations assayed, sera from 42 Brazilian dogs with a clinical diagnosis for canine leishmaniasis were tested against positive control sera from a commercial source (Bordier Affinity Products, S. A., Crissier, Switzerland) and 10 negative controls from a pathogen-free, canine research colony (College of Veterinary Medicine, North Carolina State University, Raleigh, N.C., USA).

EXAMPLE 2

Antigen Preparation

The Leishmania soluble antigen (exo-antigen) preparation was made by cultivating Leishmania promastigotes in normal supplemented media (RPMI, MEM plus FBS) at 26° C. until the culture reached mid-log phase at a density of about $10^9$ cells/ml. Then the cells were pelleted and washed 6 times in a defined, protein-free medium such as XOM available from GIBCO BRL, formula number 96–0051DJ, RPMI Medium 1640 comprising D, xylose at 0.076 mM, Hepes buffer at 25 mM, L-glutamine, and sodium bicarbonate at 30 mM without phenol red.

The cells were then resuspended in protein-free medium such as XOM to a final density of $10^8$ promastigotes/ml and incubated at 26° C. in a roller bottle with 0.01% Tween 80 (Sigma Chemical Co., St. Louis, Mo.) for 72 hours. The cells were pelleted by centrifugation at 9,000× g for 30 minutes and the supernatant was collected. The relative protein concentration of the soluble antigens was estimated by measuring the optical density at 280 nm. The antigen may be stored at 4° C.

EXAMPLE 3

Antibody and Conjugate Production

The *leishmania* soluble antigen preparation produced by the method explained in Example 2 was used without an adjuvant to immunize rabbits. The antiserum was pooled and affinity-purified on a Protein A column containing the antigen preparation of Example 2 above. Fractions of the polyclonal antibody (PAb) were conjugated with an appropriate reporter system such as horseradish peroxidase, fluorescein and colloidal gold. These tagged antibodies may then be used in antigen-detection immunoassays such as ELISA, histochemical stain and dipstick test formats. These test formats may be used to detect parasite antigens in tissues and body fluids of mammalian hosts and vectors.

Figure 7:
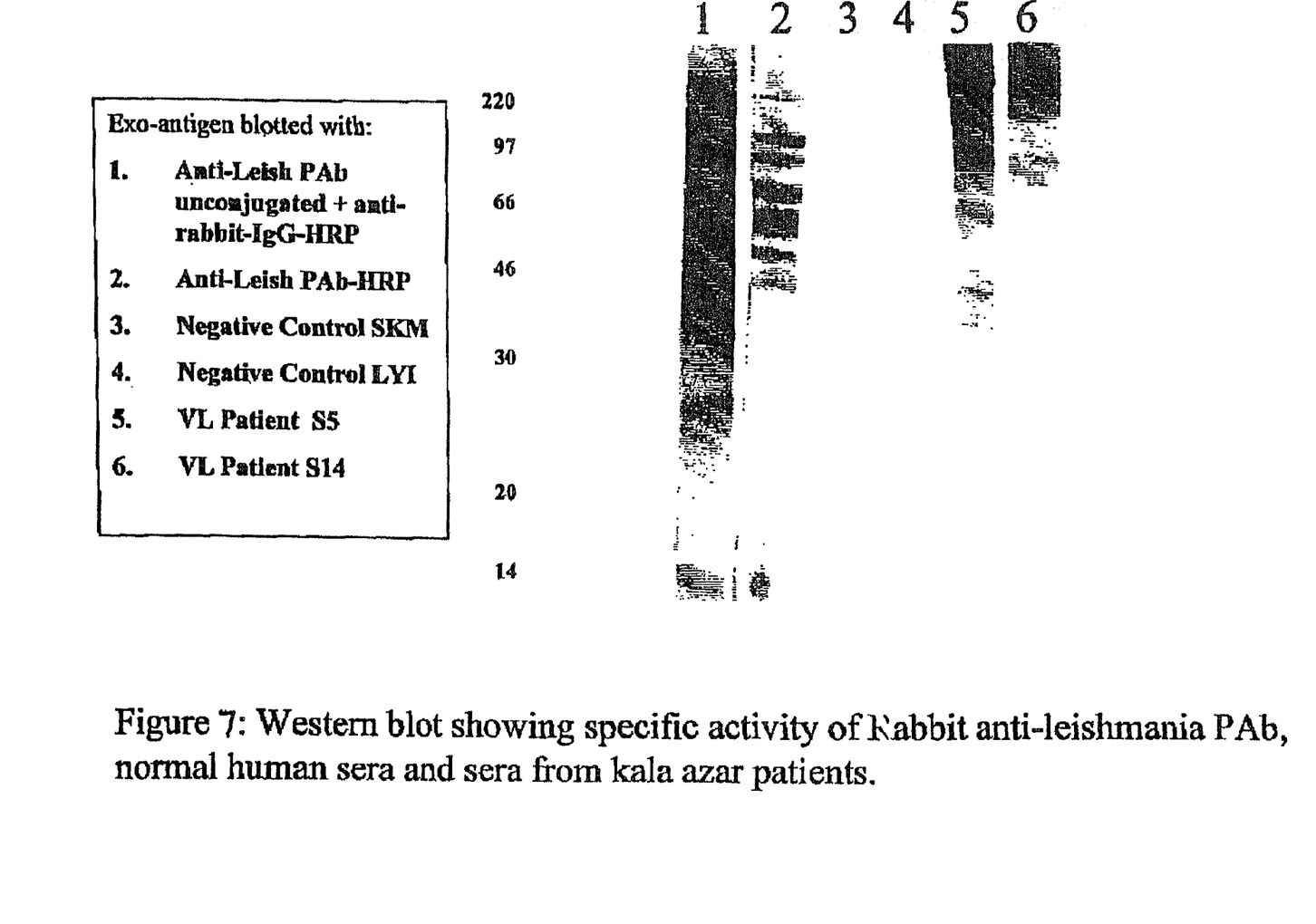
FIG. 7 is a Western Blot illustrating the striking rabbit pattern (lanes 1 and 2) similar to that of the kala azar patients pattern (lanes 5 and 6).

The rabbit anti-leishmania polyclonal antibody preparation demonstrated high affinity and avidity for the immunogens used to immunize the rabbits. The PAb produced a very striking Western Blot pattern similar to that of kala azar patients. See FIG. 7.

It is appreciated that the present invention also encompasses monoclonal antibodies against leishmania soluble antigens, hybridomas producing such, and methods of making and using thereof. Thus, monoclonal antibodies against leishmania soluble antigens may be used in the assays described herein. The monoclonal antibodies may be made by standard methods known in the art.

EXAMPLE 4

Antibody-Capture Enzyme-Linked Immunosorbent Assay

Generally, in the solid phase enzyme immunoassay for *Leishmania*, soluble antigens of the *Leishmania* promastigotes were coated on the inner surface of a test well which serve to bind specific antibody from a sample. Peroxidase conjugated antibody to anti-human IgG was added and reacted with bound antibody. A chromogenic substrate, such as horseradish peroxidase, for peroxidase was added. If antibody to *Leishmania* was present, there was a reaction that resulted in the development of color. Other fluorescent, chemiluminescent and chromogenic agents may be used with appropriate enzymes and substrates.

Plate sensitization was affected by coating a polystyrene, 96-well microtitre plates (Immulon 4, Dynatech Laboratories, Chantilly, Va.) with 100 μl of the respective exo-antigen solution (5 μg protein per well). *L. donovani* (Walter Reed reference strain 130, clone E) exo-antigen was used to sensitize plates for visceral and canine leishmaniasis samples, and *L. mexicana* (ATCC strain 50157) exo-antigen was used to sensitize plates for cutaneous leishmaniasis samples. Positive and negative controls were diluted at the same ratio as the sample. The dilutions were then placed in the wells of the microtitre plate. The samples were covered and incubated for 1 hour at room temperature in a humid environment.

Each plate was then blocked with 1.0% casein (Sigma Chemical Co., St. Louis, Mo.) in PBS for one hour at room temperature. The blocking buffer was removed by aspiration and the serum samples (100 μl of 1:1000 dilution) and appropriate controls were added to the microtiter plate and the plate was incubated at 26° C. for 40 minutes. The plate was washed with 0.05% PBS-Tween-20 (PBS-Tween) buffer four times. Preferably, an automatic plate/strip washer is used. The well contents were shaken out at the end of the final wash. Then goat anti-human IgG (whole molecule) conjugated with horseradish peroxidase (Kirkegaard & Perry Laboratories Inc., Gaithersburg, Md.) was added at 1:5000 dilution and then the plate was incubated at 26° C. for an hour in a humid environment.

The plate was then washed four times with PBS-Tween buffer and 100 μl of TMB substrate (KPL. Inc., Gaithersburg, Md.) was added to each well. The plate was incubated for about 15 minutes in the dark. The optical density (OD) was periodically read at 650 nm wavelength in an ELISA plate reader (Molecular Devices, Menlo Park, Calif.) until the OD value of a reference positive control (S5, Kala azar patient, Nepal) reached 0.8. At this point 100 μl of a stop solution (0.1M phosphoric acid) was applied to each well and the final OD reading was taken immediately at 450 nm. Preferably, a dual beam ELISA reader is used.

A reference positive serum was used in all plates, and only interassay variation of less than 10% was accepted. The lower limit of positivity (cut off) was determined by the mean of the negative controls subset+3 standard deviations.

A. Visceral Leishmaniasis.

Generally, for the test results to be accepted for visceral leishmania, the negative control must have an OD reading under 0.15 and the positive control must be over 0.8 at 650 nm. If the controls do not satisfy this criteria, the test should be repeated. Samples yielding absorbance values under 0.2 are negative and samples above 0.2 but below 0.3 may contain antibody but the amount is lower than the generally accepted significant level. It is noted that one may designate a more stringent or less stringent range for determining the absorbance levels that are indicative of exposure to leishmaniasis antigen. Samples giving absorbency values above 0.3 contain higher levels of antibody that are generally considered to be at or above the significant level.

*L. donovani* WR0130E (ATCC strain 30503) exo-antigen was used as the material to coat the microtitre plate. The negative control sera subset gave a negative cutoff score of about 0.225 for the IgG assay. With respect to specific IgG, all 129 clinically confirmed positive VL patient sera gave OD readings above the negative cutoff (100% sensitivity). When measuring IgM, the negative control sera tested gave a negative cutoff score of about 0.310. The sensitivity for this assay was 94.57% (122/129 positive).

B. Cutaneous Leishmaniasis.

Generally, for the test results to be accepted for cutaneous leishmaniasis, the negative control must have an OD reading under 0.3 and the positive control must be over 0.8 at 650 nm. If the controls do not satisfy these criteria, the test should be repeated. Samples yielding absorbance values under 0.3 are negative and samples above 0.3 but below 0.3 may contain antibody but the amount is lower than the generally accepted significant level. Again it is noted that one may designate a more stringent or less stringent range for determining the absorbance levels that are indicative of exposure to leishmaniasis antigen. Samples giving absorbance values above 0.3 contain higher levels of antibody that are generally considered to be at or above the significant level.

Figure 3:
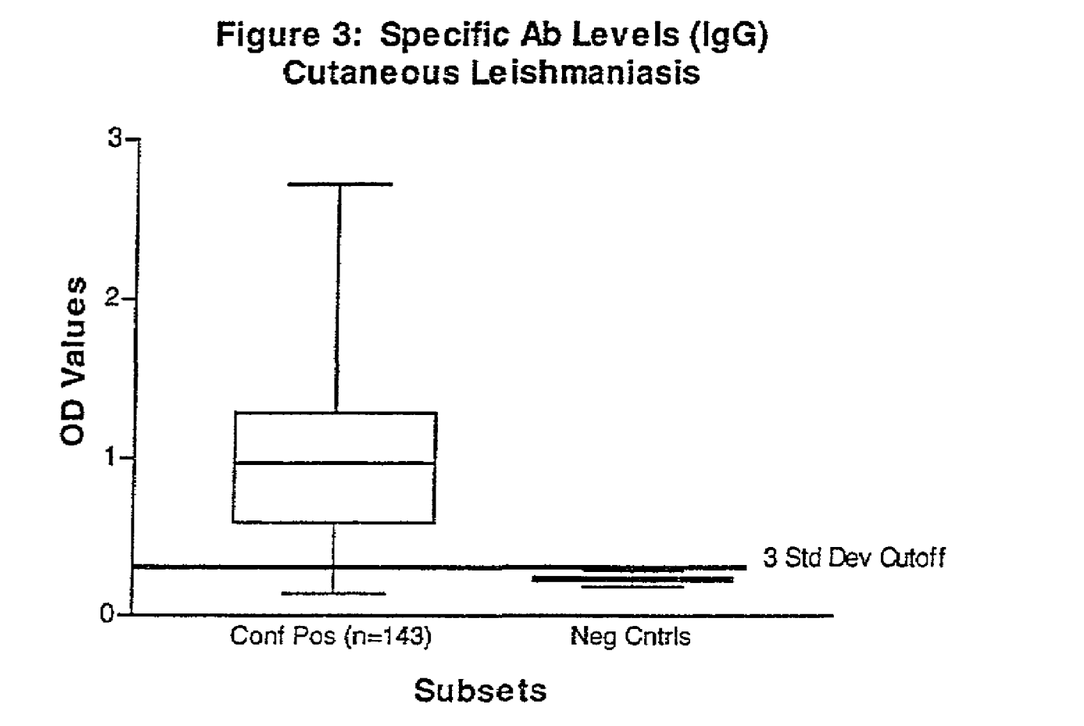
FIG. 3 is a boxplot illustrating specific IgG antibody levels measured in CL patient sera samples.
Figure 4:
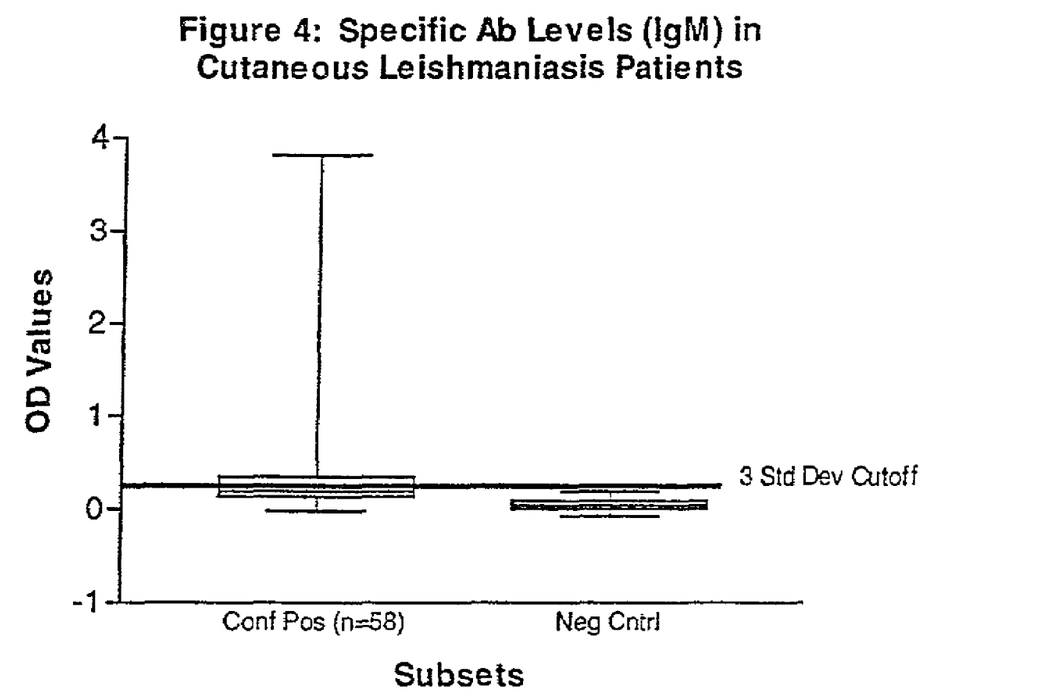
FIG. 4 is a boxplot depicting specific IgM antibody levels measured in the same samples.

*L. mexicana* exo-antigen (ATCC strain 50157) was used as the material to coat the microtitre plate. The negative control sera subset gave a negative cutoff score of approximately 0.3 for the IgG assay. The boxplot in FIG. 3 illustrates specific IgG antibody levels measured in CL patient sera samples. With respect to specific IgG, 1321143 clinically confirmed positive CL patient sera gave OD readings above the negative cutoff (92.31% sensitivity). FIG. 4 is a boxplot depicting specific IgM antibody levels measured in the same samples. When measuring IgM, the negative control sera tested gave a negative cutoff score of approximately 0.15. Only a few samples (n=6) were dramatically above the negative cutoff score, the majority of values for positive samples at or near the median value of the negative control subset. This assay failed to consistently detect specific IgM in CL patient sera samples (37.9%; 22/58 positive).

C. Canine Leishmaniasis.

Figure 5:
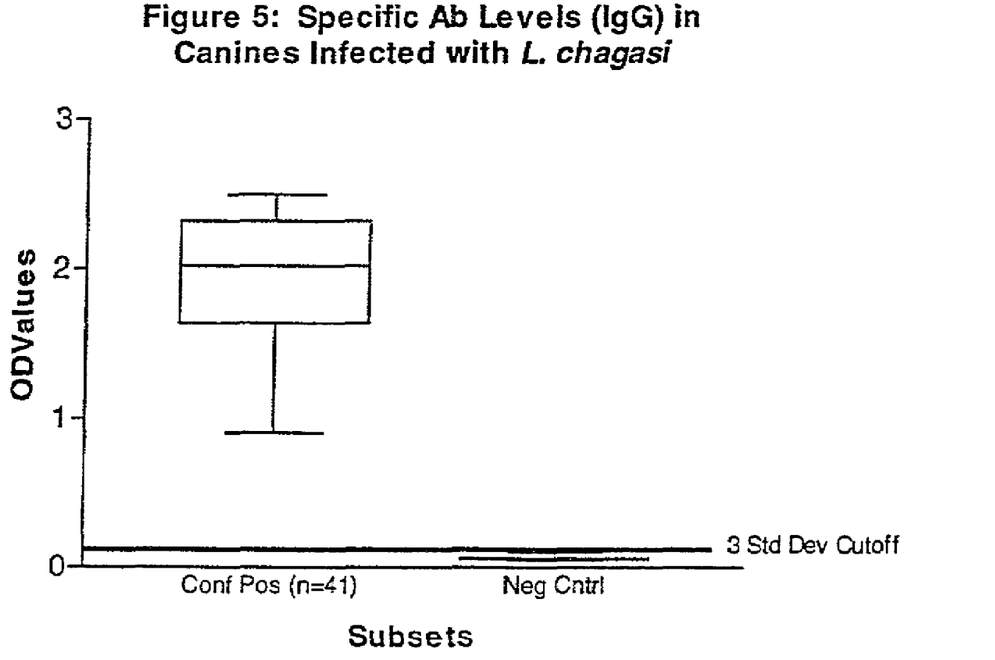
FIG. 5 shows specific IgG antibody levels measured in canine leishmaniasis sera samples.
Figure 6:
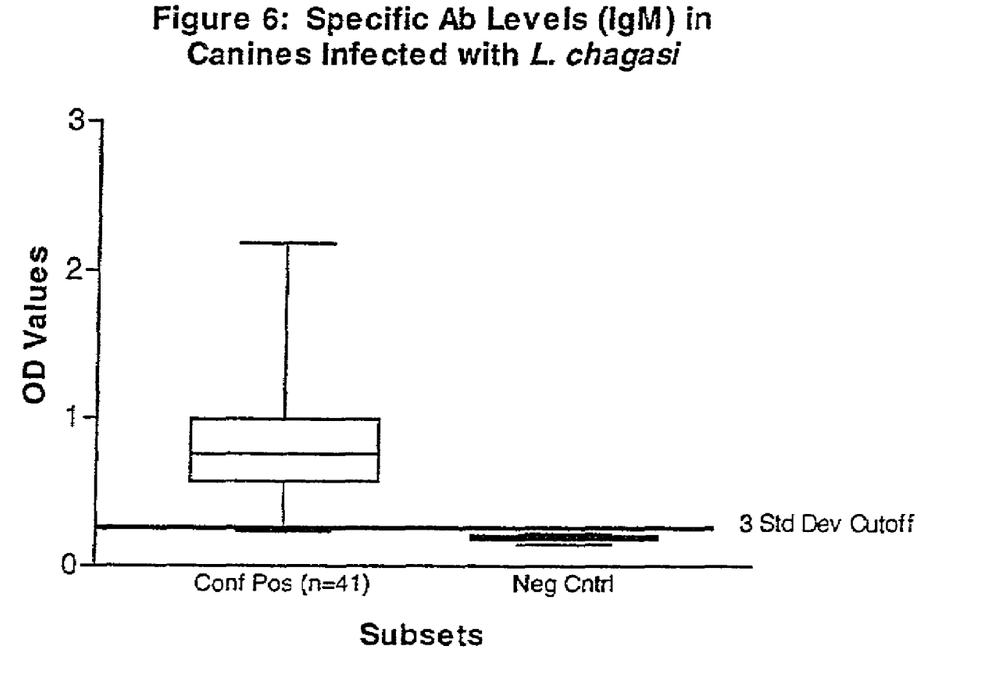
FIG. 6 is a boxplot that displays specific IgM antibody levels measured in the same samples.

*L. donovani* WR0130E (ATCC strain 30503) exo-antigen was the material used to coat the microtitre plate. The negative control sera subset gave a negative cutoff score of an OD reading of about 0.1 at 650 nm for the IgG assay. FIG. 5 shows specific IgG antibody levels measured in canine leishmaniasis sera samples. With respect to specific IgG, all 41 clinically confirmed positive canine leishmaniasis sera samples gave OD readings above the negative cutoff (100% sensitivity). Note the relatively large degree of separation between the positive and negative control subsets. The boxplot in FIG. 6 displays specific IgM antibody levels measured in the same samples. When measuring IgM, the negative control sera tested gave a negative cutoff score of approximately 0.25. The sensitivity for this assay was 97.56% (40/41).

SDS-PAGE and Western Blot analysis confirmed the ELISA results for both VL and CL patients, canine and all negative controls. Mini-Protean 11 (Bio-Rad, Hercules, Calif.) was used for SDS-PAGE. Each antigen preparation was boiled for 5 minutes in sample buffer without a reducing agent and was immediately subjected to electrophoresis on 4% stacking, 12.5% separating bis-acrylamide gels. A wide-range molecular mass marker (Bio-Rad, Hercules, Calif.) was used. An antigen load of 120 $\mu$g of protein was used in each mini-gel. The gels were run at 100 V of constant voltage for 1.5 hours in Tris-glycine-SDS buffer (pH 8.3).

Protein bands from the gel were transferred to nitrocellulose. Antigens from the SDS-polyacrylamide gels were electroblotted onto 0.45 $\mu$m pore size nitrocellulose membranes (Bio-Rad, Hercules, Calif.) with standard transfer buffer (0.02 M Tris, 0.15 M glycine, 0.1% SDS, 20% methanol) and 250 mA of constant current for 1 hour at 4° C. Following the blotting, portions of the membranes containing the protein markers were stained with 0.5% Amido black for 5 minutes and were destained in distilled water—glacial acetic acid solution. The membranes were immediately blocked with a 2% skim milk TTBS (100 mM Tris, 0.9% NaCl, 0.1% Tween 20) solution and kept refrigerated until use.

Detection of antibodies from subject sera bound to the antigens of the Western blot was done with an avidin-biotin-alkaline phosphatase system by methods standard in the art. Strips 4 mm wide were cut from previously blotted and blocked membranes. These strips were incubated with diluted sera (1:3,200 in TTBS) for 30 minutes at room temperature with constant agitation. After incubation with the primary antibody, the strips were washed 4 times for 10 minutes each time with TTBS. After the last wash, biotinylated, anti-human immunoglobulin G was added and the mixture was incubated for 30 minutes under the same conditions as described above. Preformed avidin-biotin-alkaline phosphatase complex was added. The mixture was then incubated under the same conditions as above. The membranes were developed with a BCIP/NBT substrate (Kirkegaard & Perry Laboratories, Gaithersburg, Md.) for 5 minutes. The reaction was stopped by rinsing the strips with distilled water and then adding PBS-EDTA (20 mM).

EXAMPLE 5

Antigen-Capture Enzyme-Linked Immunosorbent Assay

A. General Antigen-Capture ELISA.

An antigen-capture ELISA ("sandwich" ELISA) format based on the same soluble antigens and their complementary antibodies was developed to detect active infection in vertebrate hosts and sand fly vectors.

The capture polyclonal antibody was adsorbed to the wells of a microtiter plate. After the capture polyclonal antibodies were bound to the plate, the well contents were aspirated and the remaining active binding sites on the plates were blocked with blocking buffer. A sample such as patient sera, urine, or ground sand flies was then tested. Test samples were appropriately diluted with blocking buffer and an aliquot was tested. Sand flies to be tested were ground in blocking buffer with Nonidet P-40 (ELISA grade Sigma casein, bovine milk) and an aliquot was tested. Positive and negative controls were also added.

If parasite antigen was present it formed antigen-antibody complexes with the polyclonal sera used to coat the plate. After a 2-hour incubation, the sample was aspirated and the wells were washed. The peroxidase-linked polyclonal sera were then added to the wells, thereby completing the formation of the sandwich. Other chromogenic agents such as colloidal gold and FITC may be used with their corresponding substrates.

After 1 hour, the well contents were aspirated, the plate was washed and a clear peroxidase substrate solution from Kirkegaard & Perry Laboratories (Gaithersburg, Md.) was added. As the peroxidase enzyme reacted with the substrate a dark product was formed, which the intensity of its color was relative to the amount of circulating antigen present in the test sample. Quantitative results were obtained by making an endpoint determination a few minutes after the substrate has been added by measuring the optical density of the well contents at 450 nm with an ELSIA plate reader. However, qualitative results may be read visually in the field. ELISA positive samples may be retested to confirm positives and to estimate the amount of circulating antigen per sample.

Recently, the antigen-specific, conjugated polyclonal antibodies were used in combination with unconjugated PAb and monoclonal antibodies (MAb) specific for leishmanial Secretory Acid Phosphatases (S-cAcP) to develop a simple antigen-capture assay. The sensitivity of this assay was tested with serial dilutions of the antigen preparation prepared from the method explained above. Specific activity was recorded with the use of an HRP conjugate at a 1:32,000 dilution. The level of sensitivity in measuring these antigens with PAb was 400 ng/ml.

B. Rapid Wicking Assay.

A rapid wicking assay, based on the dual "sandwich" ELISA, was developed. The assay is conducted by placing a dipstick impregnated with immobilized polyclonal antibodies from rabbits immunized with the soluble antigen (Cellabs Pty, Ltd. Sydney, Australia) into a test solution. When soluble leishmanial antigen is present in the solution, it binds to a specific antibody with a gold sol particle label. As the antigen-antibody-gold complexes migrate through a test zone on the dipstick comprising immobilized polyclonal antibodies from rabbits immunized with the soluble antigen (Cellabs Pty, Ltd. Sydney, Australia), they bind to the corresponding immobilized antibodies to form a "sandwich". The unbound dye complexes migrate out of the test zone and can be captured later in a control zone. A reddish-purple line develops in the specific area of the test zone when antigen is present. A control line in the control zone should develop provided that the test was conducted correctly.

The test zone comprises immobilized polyclonal antibodies from rabbits immunized with the soluble antigen (Cellabs Pty, Ltd. Sydney, Australia). The control zone comprises antibodies to immobilized polyclonal antibodies from rabbits immunized with the soluble antigen (Cellabs Pty, Ltd. Sydney, Australia). Monoclonal antibodies against the soluble antigen may be used.

The test samples may be sand flies or other organisms comprising leishmania parasites ground up in a solution such as PBS with 0.5% casein. Alternatively the test samples may be blood, serum, urine, mucus, tears, stool or the like, obtained from a subject. When the test sample is urine, it is preferably undiluted.

EXAMPLE 6

In vitro Direct Immunofluorescence Test

Fluorescein-labeled polyclonal antibodies raised against specific antigens of *Leishmania* parasites may be used in an in vitro direct immunofluorescence assay. The labeled antibody binds specifically to the antigens present on the surface of the parasite which can be detected in a variety of smears such as vector specimen, in vitro culture material and patient biopsy smears.

Smears were prepared on glass slides and fixed with methanol. Unbound antibodies were removed by washing. When viewed under a fluorescence microscope, *Leishmania* parasites were seen as bright apple-green organisms characteristic to their life cycle stages contrasted with the reddish brown color of counterstained material. Promastigotes in the vectors or in culture were detected by their characteristic long and slender body (about 20 $\mu$m in length) with an anterior flagellum. Amastigotes present in clinical samples were detected by their characteristic round or oval shape measuring about 2–5 $\mu$m in diameter.

Generally, sample smears were prepared on slides marked with wells or on plain glass slides. Suitable smears had adequate specimen and were moderately thin. For sample smears prepared on a single well slide, an adequate amount of fluorescein-labeled purified polyclonal antibody diluted in a protein stabilized buffer solution (pH 7.4) with Evans Blue as a counter stain and 0.1% w/v sodium azide was added to the fixed sample smear and positive control.

For smears prepared on plain glass slides, after drying, the smear was pretreated by dipping the slide in a Coplin jar containing 0.1% sodium deoxycholate prepared in 0.85% NaCL for 5–10 minutes. The smear was air-dried. Then an adequate amount of fluorescein-labeled purified polyclonal antibody diluted in a protein stabilized buffer solution (pH 7.4) with Evans Blue as a counter stain and 0.1% w/v sodium azide was added to the fixed sample smear and positive control.

The slides were incubated at 37° C. in a moist chamber for 30 minutes in the dark. Then the slides were rinsed in a saline bath for about 2–5 minutes. The slides were allowed to air dry and then mounted with coverslips. With a fluorescence microscope under oil immersion, the slides were read.

This test format was found to be very sensitive to detecting amastigotes in infected patient tissues from subjects with cutaneous leishmaniasis infected with *L. brasiliensis* and splenic aspirates from subject with visceral leishmaniasis infected with *L. donovani*. It may be used to highlight surface antigens and cellular structure in cultured promastigotes. Preliminary results from gene cloning experiments with the *L. donovani* clone used to produce the exo-antigen indicate that one of the major immunogens in the sensitization of the rabbits used to generate the PAb is a major surface antigen.

EXAMPLE 7

Competitive ELISA

Microtiter plates were coated with the anti-leishmania PAb and blocked with 1% yeast extract. The exo-antigen was labeled with HRP. The resulting exo-antigen conjugate was mixed 1:1 with samples and applied to the plate and incubated overnight at 4° C. The plate was washed 3 times with PBS and a substrate, ABTS, was applied. The optical density of the samples were read at 405 nm.

Figure 8:
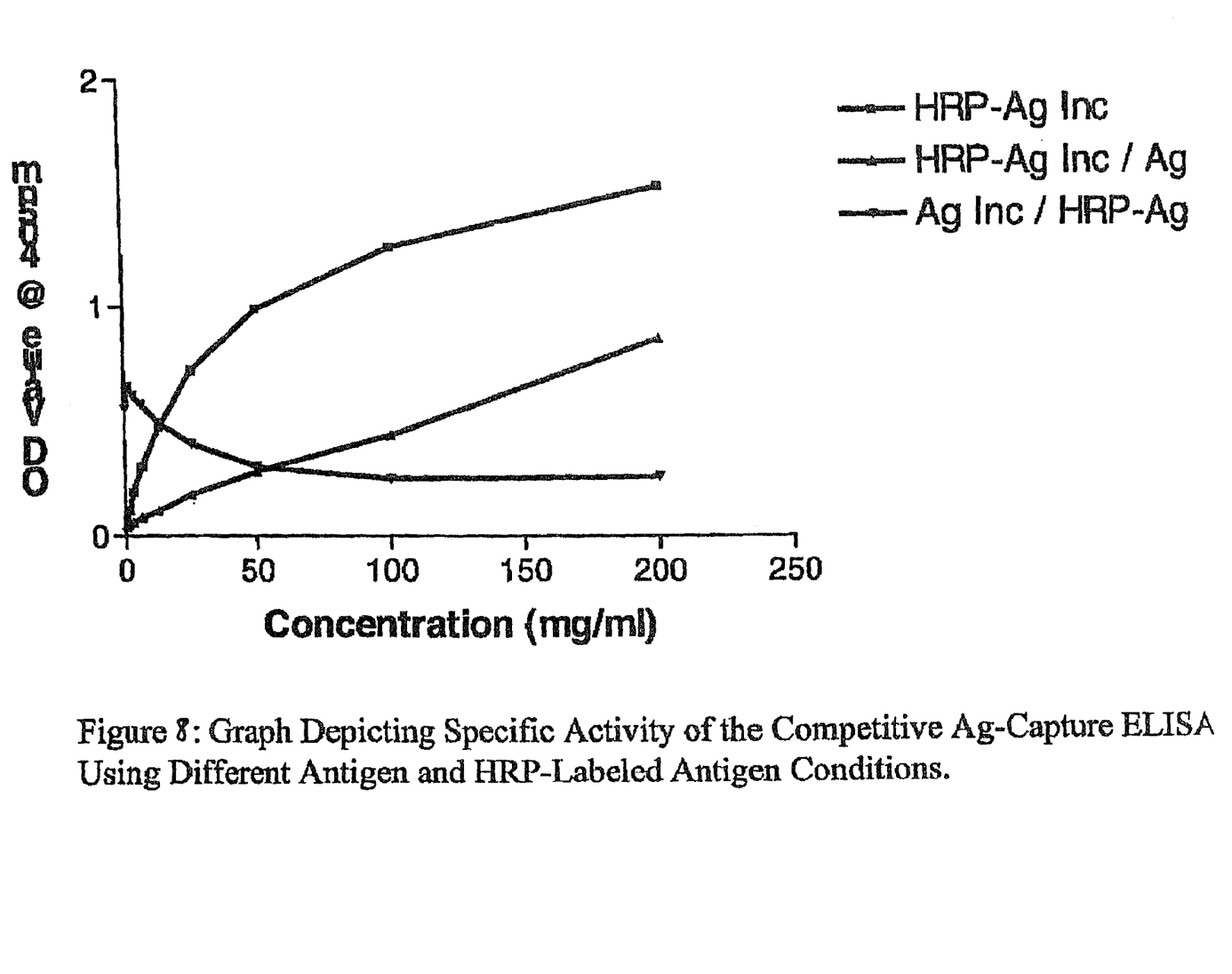
FIG. 8 is a graph illustrating the specific activity of the competitive Ag-capture ELISA while using different antigen and HRP-labeled antigen conditions.
Figure 9:
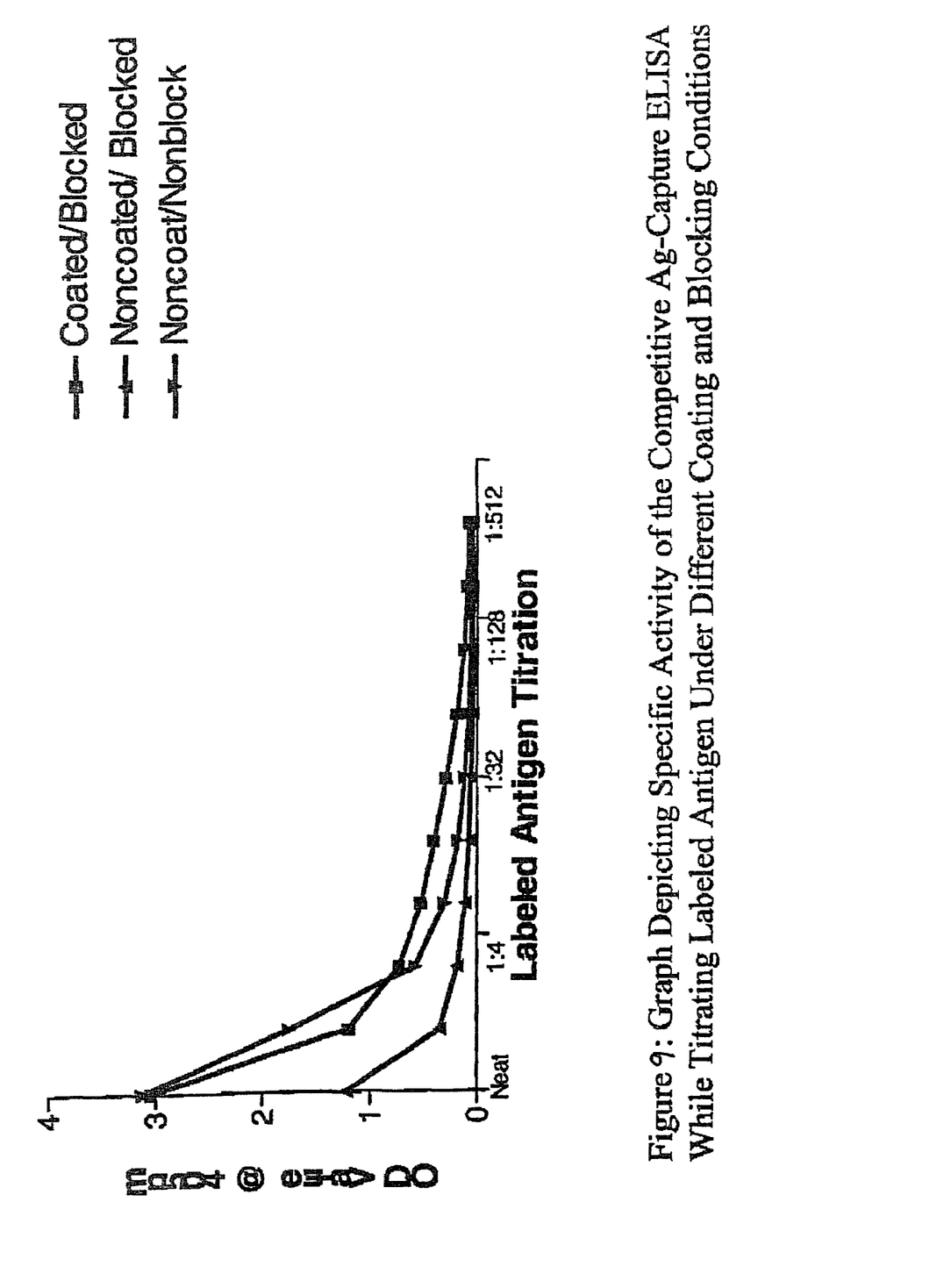
FIG. 9 is a graph illustrating the specific activity of the competitive Ag-capture ELISA while titrating labeled antigen under different coating and blocking conditions.

The competitive ELISA format worked to indirectly detect free antigen in samples. There was a correlation between increasing amounts of antigen in the samples and reduced optical density values. Further experiments were conducted to demonstrate that this relationship remained intact when varying the amount of the labeled or unlabeled antigen in the test sample and to demonstrate the importance of coating and blocking wells prior to sample incubations. See FIGS. 8 and 9.

EXAMPLE 8

Assay Optimization

The antibody detection ELISA may be optimized for diagnosis of visceral and cutaneous leishmaniasis. For example, for assay optimization for VL, the antigens released by *L. donovani* promastigotes (WHO Reference Strain 065) in vitro at 26° C. for 72 hours into serum-free and protein-free medium were obtained as described in Martin et al., (1998) and used. The soluble antigens were separated by SDS-PAGE using 4–15% Novex gradient gels (Novex, San Diego, Calif.). The proteins were visualized by colloidal Coomassie blue G-250 and silverstaining. The molecular weights of the secreted antigens were estimated with the reference to a prestained standard (Novex, San Diego, Calif.).

Titration and checker-board analyses were performed to optimize the assay protocol. Optimal results were obtained when antigen (50 $\mu$g/ml) was coated with PBS-methyl glyoxal buffer and the wells were blocked with 0.5% casein. It was found that a serum dilution of 1:500 in antigen-coated wells blocked with 0.5% casein generated lowest absorbance with negative control sera and higher absorbance with positive sera, sera from well-characterized, culture positive case subjects (used as reference positives).

An equal number of sera from North American naives with no travel history to leishmania endemic areas were used as reference negatives, negative controls or negative sera. These sera samples were used as reference samples to optimize the assay. The reference sera were not pooled and were used as individual data points. After optimizing the assay, individual sera samples obtained from endemic areas of N. Africa were screened and used to show assay performance in terms of specificity and sensitivity.

Two ELISA plates, Greiner (Greiner Labortecnik ELISA plate Cat # 705071) and Labsystem (Labsystem combiplate breakable 8 Cat #95029400), were evaluated.

The following four different coating buffers (a) 0.2M carbonate/bicarbonate buffer pH 9.6, (b) 0.01M phosphate buffer ($PO_4$) pH 7.2, (c) blank culture medium (serum-free) pH 7.2, and (d) 0.1M phosphate buffered saline (pH 7.2)+1% methyl glyoxal were tested for their ability to immobilize the antigen onto the solid phase ELISA wells.

Gelatin ranging in concentration from 0.1 to 0.4% solution and 0.5% casein were tested. BSA and other routinely employed blocking agents were not tested because of nonspecific binding noted in previous experiments.

PBS/T and PBS/T+0.2M NaCl were used as the washing buffers. An automatic plate washer (Denley Well Wash 04) with 4 cycle wash in each step was used to wash the ELISA wells. In most of the assays the wash buffer was used as the diluent for sera as well as the conjugated detector antibody.

Two anti-human IgG conjugated to HRP (HRP conjugate) were tested. A goat anti-human IgG-HRP (Kirkegaard & Perry Laboratories, Gaithersburg, Md.), a polyclonal conjugate (PAb conjugate), and a mouse anti-human IgG-HRP (Cellabs, Brookvale, Australia), (MAb conjugate).

All steps of the ELISA were performed at room temperature. The S/N ratio, the differential absorbance between the negative sample versus the test or positive sera sample, was used to quantify the specific antigen and antibody reactions. An anti-human monoclonal antibody conjugated with HRP (MAb conjugate) outperformed a commercially available anti-human polyclonal antibody conjugate (PAb conjugate) (Cellabs Pty, Ltd. Sidney, Australia). The MAb conjugate gave minimal background reactions with endemic sera. Generally, the wells of an ELISA plate were coated with 50 μg/mL of the soluble antigens released by *L. donovani* promastigotes in serum-free and protein-free medium mixed in PBS-methyl-glyoxal overnight. After removing the antigen, the wells were blocked with 0.5% casein for 1 hour at room temperature. Test sera along with positive and negative control sera diluted 1:500 in PBS/T, were reacted for 1 hour at room temperature. After washing the plate with PBS/T, the wells were reacted with an HRP-conjugated anti-human antibody, the detector antibody, for 40 minutes at room temperature. The plates were washed and specific binding of antigens on the solid phase and the specific antibodies present in the test sera were measured indirectly by the binding of HRP labeled detector antibody which was further detected by using TMB+$H_2O_2$ as a chromogenic substrate.

TMB solution A and B (KPL, Gaithersburg, Md.) were mixed in equal parts 5–10 minutes before and transferred an aliquot of 100 μl to each well as per the guidelines provided by the manufacturer. During the developmental phase of the assay, the color intensity of positive sera wells was monitored (absorbance OD of 620 nm) and stop solution was added when those wells reached an OD of 0.450. In the final optimized assay, the incubation time with substrate was fixed at 25 minutes.

After adding the stop solution (1M Phosphoric acid prepared in distilled water) the contents were mixed and the plate was read at dual filter (450/620 nm) using a plate reader (Anthos LabTec Instruments 2001).

The raw data from the plate, i.e., absorbance at 450/620 nm, were plotted into histograms and graphs. The relative specific binding was quantified by the signal to noise (S/N) ratio which was calculated by dividing the mean absorbance, i.e., absorbance at 450/620 nm, of test sera with the mean absorbance of negative sera, and plotted. The S/N ratio was directly proportional to the specific antibody reactivity in ELISA. A batch of n=22 endemic sera from North Africa were evaluated and resulted with 100% specificity and sensitivity, 99.99% PPV (positive predictive values) and 95.45% NPV (negative predictive values).

The LabSystem plate did not perform well in this study. There was no discrimination between the positive and negative sera. There was a clear distinction between sera in the Greiner plate. It was found that the PBS+methyl glyoxal, phosphate buffer and culture medium respectively showed higher reactivity with positive sera and relatively less reactivity with negative sera. A higher S/N ratio was seen using sera at a 1:500 sera dilution. Phosphate buffer, culture medium and PBS-glyoxal gave higher SIN ratios. Therefore, the Greiner plate and PBS+methyl glyoxal were selected as ELISA plate and coating buffer respectively.

Using the Greiner ELISA plate and PBS+methyl glyoxal as the coating buffer for the test, positive and negative sera were used at 1:500 dilution. Two anti-human IgG-HRP conjugates were evaluated at 4 different dilutions. The PAb conjugate was found to be highly reactive with the negative sera indicating a high level of nonspecific reaction. On the other hand, the same level of reactivity was observed in the blank and negative sera sample wells with the MAb conjugate. The reactivity with MAb conjugate appeared to be more specific with positive sera as evidenced by higher S/N ratios.

Negative and positive sera were reacted at 1:500 dilution and washed with two different wash solutions. MAb conjugate was used at 1:8000 dilution. Plates were read at 450/620 nm. Reactivity of blanks and negative sera were lower in wells washed with PBS/T +0.2M NaCl. The data indicated that PBS/T +0.2M NaCl was more effective in removing non-specific binding (nearly 45% reduction of nonspecific signal 0.283 v. 0.114) and increasing the SIN ratio from 3.7 to 7.2. Despite its higher S/N ratio, 0.2M NaCl was left out of the final wash buffer because it formed a precipitate on standing.

Having selected the Greiner plate and PBS+glyoxal as the coating buffer, optimum levels of antigen and appropriate blocking reagents were investigated. Wells were coated with a series of antigen concentration from 1.25 μg/ml to 40 μg/ml. Two blocking reagents, 0.4% gelatin and 0.5% casein prepared in distilled water were evaluated. Positive and negative sera, diluted 1:500 in PBS/T, reacted in the Ag-coated and blocked wells for 1 hour at room temperature. Two conjugates, PAb and MAb-conjugates, diluted 1:4000 in PBS/T were added to wells and incubated for 30 minutes at room temperature. The color was developed for 25 minutes by adding the substrate and immediately read after addition of stopping solution. The reactivity was higher in blank and negative sera wells with PAb conjugate thereby reducing the differences between samples that resulted with a low S/N ratio. With the MAb conjugate, the absorbance of blank and negative sera wells was almost equal. There was a pattern in the reactivity relative to the antigen concentration. Wells reacted with the positive sera showed a gradual rise in absorbance dependent upon the antigen concentration. On the whole, MAb conjugate reactivity was relatively lower in control sample wells. The SIN ratios were higher with MAb conjugate when casein used for blocking. MAb conjugate with casein blocking generated excellent SIN ratios, at 20 and 40 μg/ml antigen levels.

Experiments involving the relative kinetics of antibody reactivity at different sera dilutions provided a good discrimination at 1:500 dilution. This formed the basis for future assays.

After optimizing assay steps, the following protocol was followed for evaluating test sera samples of subjects from endemic areas. In short, the wells were coated with 50 μg/ml soluble antigen mixed in PBS-methyl-glyoxal buffer overnight and after removing the antigen, the wells were blocked with 0.5% casein for 1 hour at room temperature. Test serum along with control sera diluted 1:500 in PBS/T, was reacted for 1 hour at room temperature. After washing the plate in PBS/T, the wells were reacted with MAb conjugate at 1:8000 dilution for 40 minutes at room temperature and after washing, the TMB substrate was added and color development was allowed to proceed for 25 min and then stopped with the stop solution.

Absorbance was read at dual filter (4501620 nm) and the results were analyzed. A total of n=22 test clinical sera obtained from the endemic areas of North Africa were evaluated along with n=5 reference control negative sera.

SDS-PAGE analysis was conducted Coomassie staining showed several major bands with approximate molecular weights of 11, 30, 42, 50 and 161 kDa. In addition to these abundant bands, silver staining revealed more distinct protein bands of approximately 6, 15; 17, 22, 58, and 107 kDa. This illustrates that the test contained a variety of protein antigens.

The cut-off value in the current assay was mean +3 SD of negative (n=5) sera (Mean 0.1304, SD=0.042), i.e., 0.278 which is rounded off to 0.300. Using an absorbance OD450/620 nm of 0.300 as the cut off, n=22 test sera from field were categorized as either positive or negative. With the exception of one sample, all were positive. The sensitivity, specificity, PPV and NPV were calculated. Thus, the sensitivity and specificity were both 100%, the PPV was 99.9% and NPV was 95.45%. The resultant S/N ratio of these samples suggests that the assay is highly sensitive and specific.

Clearly, one of ordinary skill in the art may further optimize the assays of the invention by changing various assay conditions by methods standard in the art.

Incorporation by Reference

To the extent necessary to understand or complete the disclosure of the present invention, all publications, patents, and patent applications mentioned herein are expressly incorporated by reference therein to the same extent as though each were individually so incorporated.

What is claimed is:

1. An immunoassay for detecting exposure to *Leishmania* parasites in a subject comprising the steps of:
   (a) culturing the *Leishmania* parasites in a protein free medium comprising an oncotic agent, xylose;
   (b) isolating a soluble antigen;
   (c) contacting a sample from the subject suspected of having leishmaniasis with the soluble antigen; and
   (d) detecting the presence or measuring the amount of an antibody in the sample bound to the soluble antigen.

2. The immunoassay of claim 1, wherein the protein-free medium further comprises at least one of the following ingredients: Hepes buffer, L-glutamine or sodium bicarbonate without phenol red.

3. The immunoassay of claim 1, wherein the antibody is IgG or IgM and is specific for a *Leishmania* antigen.

4. The immunoassay of claim 1, wherein the sample is a serum sample.

5. The immunoassay of claim 4, wherein the serum sample is modified by diluting it 1:1000 in blocking buffer having 1.0% boiled casein.

6. The immunoassay of claim 1, wherein said immunoassay is capable of diagnosing visceral, cutaneous or canine leishmaniasis in a subject.

7. The immunoassay of claim 1, wherein the *Leishmania* parasites are clones of *Leishmania donovani, Leishmania mexicana*, or a combination thereof.

8. The immunoassay of claim 1, wherein the oncotic agent balances the oncotic pressure across the semi-permeable membrane of the *Leishmania* parasites.

9. The immunoassay of claim 1, wherein the oncotic agent is a colloidal agent, a crosslinking agent, or both.

10. The immunoassay of claim 1, wherein the oncotic agent is D, xylose.

11. The immunoassay of claim 1, wherein the soluble antigen is of either *L. donovani* or *L. mexicana*.

12. The immunoassay of claim 1, wherein the soluble antigen is coated on a substrate.

13. The immunoassay of claim 1, further comprising using a positive control.

14. The immunoassay of claim 1, further comprising using a negative control.

15. The immunoassay of claim 1, further comprising using a diluent.

16. The immunoassay of claim 1, further comprising using an anti-human IgG conjugated to a label.

17. The immunoassay of claim 1, further comprising using a substrate chromogen.

18. The immunoassay of claim 1, further comprising using a substrate buffer.

19. The immunoassay of claim 1, further comprising using a blocking buffer.

20. The immunoassay of claim 1, further comprising a stopping solution.

* * * * *